United States Patent [19]

de Wied

[11] Patent Number: 4,623,640
[45] Date of Patent: Nov. 18, 1986

[54] PEPTIDES

[75] Inventor: David de Wied, LH Bilthoven, Netherlands

[73] Assignee: Akzo N.V., Arnhem, Netherlands

[21] Appl. No.: 720,704

[22] Filed: Apr. 8, 1985

[30] Foreign Application Priority Data

Apr. 13, 1984 [NL] Netherlands ................. 8401187

[51] Int. Cl.⁴ .................. A61K 37/02; C07K 5/10
[52] U.S. Cl. ............................ 514/18; 530/330
[58] Field of Search ............ 260/112.5 R; 514/17, 514/18; 530/330

[56] References Cited

U.S. PATENT DOCUMENTS 3,989,631  9/1976  Prochazka et al. ........... 260/112.5
4,487,765 12/1984  de Wied ...................... 260/112.5 R

*Primary Examiner*—Delbert R. Phillips
*Attorney, Agent, or Firm*—Wegner & Bretschneider

[57] ABSTRACT

The present invention relates to peptides having psychopharmacological properties, of the formula:

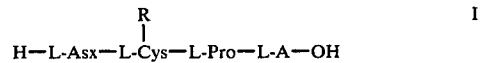

wherein
A represents the aminoacid residue Arg, Lys or Leu and
R represents

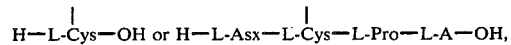

as well as the functional derivatives thereof.

7 Claims, No Drawings

PEPTIDES

The present invention relates to peptides having psychopharmacological properties, to a process for the preparation of these peptides and to a pharmaceutical preparation which contains these peptides as the active ingredient.

More especially, the invention relates to peptides which in the main are to be regarded as fragments of vasopressin and oxytocin.

Both oxytocin and vasopressin are peptides which according to their hormonal actions are also described as neuropeptides, namely as peptides which inter alia affect memory processes.

There have now been found peptides which only possess a part of the aminoacid sequence of oxytocin and vasopressin and which have a much stronger and more specific influence on memory processes, while the hormonal actions of oxytocin and vasopressin are no longer present.

Such peptides, which are derived from either vasopressin or oxytocin, have already been described in Netherlands Patent Application Nos. 82/03,949 and 82/04,881, which do not constitute a prior publication. These peptides have the aminoacid sequence 4-8 and 4-9 of oxytocin and vasopressin, except that the aminoacid residue in position 4 is a pyroglutamyl residue in place of a glutaminyl residue and that the aminoacid in position 6 is cystine (Cyt).

Since the fragment 5-9 (Cyt$^6$) of oxytocin was not that interesting in certain memory tests, it has hitherto been assumed that the aminoacid in position 4 made an essential contribution to the said action on memory processes and that therefore this aminoacid could not be omitted.

Surprisingly it has now been found, however, that the aminoacid sequence 5-8 (Cyt$^6$) of oxytocin and vasopressin still exerts an at least equally strong influence on the memory than the abovementioned (longer) fragments.

Accordingly, the present invention relates to peptides having the general formula:

$$\text{H--L-Asx--L-Cys--L-Pro--L-A--OH} \quad \overset{R}{|} \quad \text{I}$$

wherein
A represents the aminoacid residue Arg, Lys or Leu and
B represents

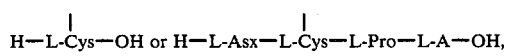

as well as the functional derivatives thereof.

The peptides and peptide derivatives according to formula I are prepared in the manner customary for peptides. A customary process for the preparation of the compounds in question is to couple the required aminoacids by means of condensation either in the homogeneous phase or, for example, in a so-called solid phase.

The condensation in the homogeneous phase can be carried out as follows:

(a) condensation of an aminoacid or peptide having a free carboxyl group and protected other reactive groups with an aminoacid or peptide having a free amino group and protected other reactive groups, in the presence of a condensation agent, (b) condensation of an aminoacid or peptide having an activated carboxyl group and optionally protected other reactive groups with an aminoacid or peptide having a free amino group and optionally protected other reactive groups, (c) condensation of an aminoacid or peptide having a free carboxyl group and protected other reactive groups with an aminoacid or peptide having an activated amino group and optionally protected other reactive groups.

Activation of the carboxyl group can inter alia be effected by converting the carboxyl group to an acid halide, an azide, an anhydride, an imidazolide or an activated ester, such as the N-hydroxy-succinimide, N-hydroxy-benztriazole or p-nitrophenyl ester.

The amino group can be activated by converting it to a phosphite-amide or by employing the "phosphorazo" method.

The commonest methods for the above condensation reactions are: the carbodiimide method, the azide method, the mixed anhydride method and the activated ester method, as described in "The Peptides", Volume I, 1965 (Academic Press) E. Schröder and K. Lübke.

The compounds according to formula I can also be prepared by the "solid phase" method (Merrifield; J.A-mer.Chem.Soc. 85, 2149 (1963)). The coupling of the aminoacids of the peptide to be prepared starts from the side having the carboxyl terminal group. For this reaction, a solid carrier whereon reactive groups are present or onto which such groups can be attached is necessary. This carrier can for example be a copolymer of benzene and divinylbenzene having reactive chloromethyl groups, or a polymeric carrier which has been made reactive with hydroxymethyl or benzylamine.

If, for example, a carrier containing chloromethyl groups is used, bonding of the first α-amino-protected aminoacid to the carrier takes place via an ester bond. In the synthesis of a peptide according to formula I, wherein A represent L-Leu, this thus in the first instance gives:

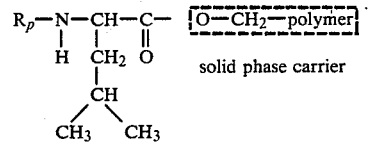

solid phase carrier wherein R$_p$ is an α-amino-protective group.

After removal of the group R$_p$ the next α-amino-protected aminoacid (in this case proline, wherein the α-amino group is protected) can for example be coupled on by a condensation reaction, and after removing the protective group from the α-amino group, the next aminoacid can be coupled on etc. In many cases it is desirable to use a significant excess of each α-amino-protected aminoacid.

After synthesis of the desired aminoacid sequence the peptide is released from the carrier by means of, for example, HF or trifluoromethanesulphonic acid. The peptide can also be removed from the carrier by transesterification with a lower alcohol, preferably methanol or ethanol, whereby a lower alkyl ester of the peptide is formed directly. Similarly, releasing with, for example, ammonia gives the C-terminal amide derivative of the peptides I.

The reactive groups which are not to participate in the condensation reaction are protected by groups which can again be removed easily, for example by hydrolysis or reduction. Thus, a carboxyl group can be protected effectively by, for example, esterification with methanol, ethanol, tertiary butanol, benzyl alcohol or p-nitrobenzyl alcohol.

Groups which can effectively protect an amino group are usually acid groups, for example an acid group derived from an aliphatic, aromatic or heterocyclic carboxylic acid, such as the acetyl, benzoyl or pyridinecarboxyl group, or an acid group derived from carbonic acid, such as the ethoxycarbonyl, benzyloxycarbonyl, t-butoxycarbonyl or p-methoxybenzyloxycarbonyl group, or an acid group derived from a sulphonic acid, such as the p-toluenesulphonyl group, but other groups can also be used, such as substituted or unsubstituted aryl or aralkyl groups, for example benzyl and triphenylmethyl, or groups such as ortho-nitro-phenyl-sulphenyl or 2-benzoyl-1-methylvinyl.

It is advisable that the ε-amino group of lysine and the guanidine group of arginine should also be protected. Customary protective groups in this context are a tertiary butoxycarbonyl group or a tosyl (Tos) group for lysine and a nitro group, Mbs group, Tos group or Pms group for arginine.

Though in the aminoacid condensations referred to above the aminoacid cystine can be used, it is nevertheless preferable in the first instance to use the aminoacid cysteine, wherein the thiol group (—SH) is protected by means of a customary SH-protective group such as acetamidomethyl or trityl. After the complete desired aminoacid sequence (with cystinyl in place of cystinyl) has been synthesised, the thiol group of the cysteinyl radical present in the peptide is thereafter—optionally following separate removal of the thiol-protective group—coupled in a known manner to the thiol group of a second cysteine molecule or to the thiol group of a second molecule of the same peptide.

The protective groups can be split off in accordance with various conventional methods, depending on the nature of the group in question, for example with the aid of trifluoroacetic acid or methanesulphonic acid.

By functional derivatives of the peptides according to the general formula I there are meant:

1. salts of the peptides in question, in particular the pharmaceutically acceptable acid addition salts and metal salts;
2. N-acyl derivatives derived from an aliphatic carboxylic acid having 1-6 carbon atoms, and preferably acetic acid;
3. amides or monoalkyl- or dialkyl-substituted amides in which the alkyl group has 1-6 C-atoms;
4. esters derived from alcohols having 1-18 C-atoms and preferably from aliphatic alcohols having 1-6 C-atoms.

The acid addition salts can be obtained directly by isolating the peptide from the desired acid medium or the peptide obtained can subsequently be converted to an acid addition salt by reaction of the peptide with an acid such as HCl, HBr, phosphoric acid, sulphuric acid, acetic acid, maleic acid, tartaric acid, citric acid or polyglutamic acid.

The metal salts, namely the alkali metal salts, are obtained by reacting the peptide with the desired metal base, such as NaOH, $Na_2CO_3$, $NaHCO_3$ etc. or, in the "solid phase" method, by releasing the peptide from the solid carrier with an alkali metal hydroxide.

N-acyl derivatives, whereby in particular the N-terminal acyl derivatives are meant, are preferably prepared by using an aminoacid which is already provided with the desired acyl group. This acyl group then also functions as a protective group in the peptide synthesis. In this way, the desired acyl derivative is prepared directly. It is, however, also possible to introduce the desired acyl group after the peptide synthesis by acylating the peptide in a usual manner.

The preferred N-acyl group is the acetyl group.

Esters and amides of the peptides according to formula I are, preferably prepared by using, (in the peptide synthesis according to the homogeneous condensation method), an aminoacid which is already provided with the desired ester or amide group; they can, however, also be prepared by subsequently esterifying the peptide obtained, or converting it to an amide, these reactions being carried out in the usual manner. In the "solid phase" method, esters can be obtained by trans-esterification of the peptide-solid phase combination, and amides can be obtained by treatment with ammonia.

Preferably, the lower aliphatic esters derived from an alkanol having 1-6 C-atoms are used, such as the methyl, ethyl, propyl, isopropyl, butyl, sec.-butyl, pentyl or hexyl ester.

Amides which are used preferably are the unsubstituted amide, the monomethyl-amide, the dimethyl-amide, the monoethyl-amide or the diethyl-amide.

The peptides according to the invention have, as already mentioned above, a psychopharmacological action and in particular exert an influence on memory processes; this influence is marked and is, surprisingly, stronger than that of known neuropeptides such as oxytocin and vasopressin.

Peptides according to the present invention wherein A represents L-Lys or L-Arg greatly promote the consolidation and the retrieval of the memory and can in general be used in cases where a stimulation of memory processes (or the mental performance) is desired, such as in the treatment of depressions, but in particular in the treatment of disturbances in learning processes and memory processes such as for example may occur in the elderly (senility).

Peptides according to the invention wherein A represents L-Leu inhibit the consolidation and retrieval of the memory. These peptides should in general be used in cases where an inhibition of the central nervous system and in particular of learning and memory processes is desirable; they can in general be used as, for example, sedatives and more especially in the treatment of obsessional neuroses.

Peptides of the formula I which are to be preferred are those wherein Asx represents asparaginyl.

The peptides according to the invention can be administered orally, rectally, parenterally, sublingually or intranasally. Parenteral and intranasal administration are to be particularly preferred in that in these cases the absorption of the peptide is greatest. For this purpose, the peptides are preferably mixed with pharmaceutically acceptable auxiliaries which make the peptides suitable for parenteral or intranasal administration, resulting in solutions, suspensions (optionally via microencapsulation), emulsions and sprays.

Mixed with suitable auxiliaries or fillers the peptides in question can also be used in a form suitable for oral administration, such as pills, tablets and coated tablets.

The peptides in question can also be administered in the form of a suppository.

The peptides or peptide derivatives according to the invention are preferably used in a dosage of 1 ng to 5 μg per kg of body weight per day for parenteral or intranasal administration. The recommended dosage for human administration is between 1 and 100 μg per day. For oral and rectal administration the dosage is in general higher by a factor of 10–100.

With regard to the examples, the following should be noted.

I. Where no optical configuration is indicated, the L-form is meant.

II. The following abbreviations are used for the protective or activating groups used:
 Scm=S-carbomethoxysulphenyl
 tBu=tertiary butyl
 Boc=tertiary butoxycarbonyl
 Mbs=4-methoxybenzenesulphonyl
 Pms=pentamethylbenzene sulphonyl
 Me=methyl
 Trt=trityl III. The following abbreviations are used for the solvents or reagents employed:
 EtOH=ethanol
 BuOH=butanol
 Py=pyridine
 HOAc=acetic acid
 t.BuOH=tert.-butanol
 MeOH=methanol
 DMF=dimethylformamide
 THF=tetrahydrofuran
 DCC=dicyclohexylcarbodiimide
 DCU=dicyclohexylurea
 TFA=trifluoroacetic acid
 To=toluene
 HOBt=N-hydroxybenzotriazole IV. The following abbreviations are used for the aminoacid groups:
 Lys=lysyl
 Arg=arginyl
 Pro=prolyl
 Cys=cysteinyl
 Asx=aspartyl or asparaginyl
 Asp=aspartyl
 Asn=asparaginyl
 Cyt=cystinyl
 Leu=leucyl

EXAMPLE 1

1. Boc-Asn-Cys(Trt)-Pro-Arg(Mbs)-OtBu 3.00 g (3.56 millimoles) of H-Cys(Trt)-Pro-Arg(Mbs)-OtBu and 0.83 gg (3.56 millimoles) of Boc-Asn-OH were dissolved in 30 ml of DMF and cooled to −20° C. At this temperature, 0.58 g (4.27 millimoles) of HOBt and 0.81 g (3.92 millimoles) of DCC were added and the mixture was stirred for 1 hour. Thereafter it was stirred for a further hour at 0° C. and overnight at room temperature, after which the DCU formed was filtered off. The filtrate was evaporated and the residue dissolved in 100 ml of a 3:2 methylene chloride/2-butanol mixture. Thereafter the solution was extracted successively with 3×30 ml of 5% NaHCO₃, 3×30 ml of 5% KHSO₄ and 3×30 ml of 30% NaCl solutions. The organic layer was dried with Na₂SO₄ and the peptide was precipitated by adding ether.

Yield 3.25 g. The Rf is 0.22 in an 8:2 To:EtOH mixture; $[\alpha]_D^{20}=-1.9°$ c=1, DMF).

2. Boc-Asn-Cys(Scm)-Pro-Arg(Mbs)-OtBu 3.00 g (2.84 millimoles) of Boc-Asn-Cys(Trt)-Pro-Arg(Mbs)-OtBu (1) were dissolved in a mixture of 10 ml of methanol and 50 ml of methylene chloride. 0.4 ml of Scm-chloride was added with stirring and after 5 minutes the substance was precipitated with ether. The precipitate was filtered off and was then washed with ether and dried.

Yield 2.56 g; $[\alpha]_D^{20}=-66.9°$ (c=1, DMF).
Rf=0.17 in an 8:2 To:EtOH mixture.

3.

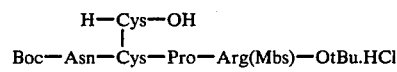

2.40 g (1.47 millimoles) of the peptide obtained in 2., in 200 ml of ethanol, were introduced into a flask containing 650 mg (3.71 millimoles) of H-Cys-OH.HCl.H₂O in 10 ml of methanol, under nitrogen and with stirring. The mixture was then stirred for a further 40 minutes. The solution was evaporated and the peptide was precipitated with ether. The precipitate formed was then filtered off and dried. Yield 2.48 g. The peptide was then dissolved in a 2:3 mixture of 2-butanol/methylene chloride and the solution was extracted with water. The peptide in the organic layer was precipitated and the precipitate was filtered off and dried. Yield 850 mg.

The Rf is 0.52 in a 70:30:5 methylene chloride:methanol:water mixture.

4.

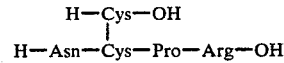

850 mg ( ) 0.88 millimole) of the peptide obtained in 3. were dissolved in a mixture of 15 ml of TFA and 2.2 ml (35.2 millimoles) of MSA and 0.2 ml of thioanisole and the solution was stirred for 5 hours. The reaction mixture was poured into ether and the precipitate formed was filtered off and washed with ether. Thereafter the precipitate was dissolved in a 1:1 tert.-butanol/water mixture, subjected to exchange with an ion exchanger in the acetate form, and freeze-dried. Yield 639 mg. The substance was then purified with the aid of a silica gel column, using butanol/acetic acid/water (2:1:1) as the eluant. Yield 315 mg.

$[\alpha]_D^{20}=-136.3°$; (=0.25; 10% HOAc).

EXAMPLE 2

1. Boc-Asn-Cys(Trt)-Pro-Leu-OtBu 2.50 g (2.86 millimoles) of Trt-Cys(Trt)-Pro-Leu-OtBu were dissolved in 25 ml of acetic acid, after which 2.5 ml of water were added. The mixture was then stirred for 1 hour, after which 10 ml of water were added and the precipitate formed was filtered off. The solution which remained was then evaporated and the residue dissolved in ethyl acetate, after which the solution was washed with 3×50 ml of 5% NaHCO₃ solution and 3×saturated NaCl solution. The organic layer was dried and then evaporated. The residue was dissolved in 25 ml of DMF, after which 655 mg (2.86 millimoles) of Boc-Asn-OH were added. The mixture was cooled to −15° C., after which 464 mg (3.43 millimoles) of HOBt and 651 mg (3.15 millimoles) of DCC were added in succession. When the mixture had been stirred for some time it was cooled further to −25° C., after which DCU was filtered off and the solution was evaporated. The residue was dissolved in 50 ml of ethyl acetate and washed with 3×25 ml of 5% NaHCO$_3$ solution, 3×25 ml of 5% KHSO$_4$ solution and 3×25 ml of saturated NaCl solution. The organic layer was then dried over Na$_3$SO$_4$ and evaporated. After the residue had been dissolved in ether, the peptide crystallised out. These crystals were then filtered off and dried.

Yield 1.64 g; melting point 127°–128° C.; $[\alpha]_D^{20} = -18.1°$ (c=1, DMF).

2. Boc-Asn-Cys(Scm)-Pro-Leu-OtBu 1.50 g (1.78 millimoles) of the peptide obtained in 1. were dissolved in 10 ml of methylene chloride after which 0.3 ml of Scm-chloride was added. After the mixture had been stirred for 5 minutes, the precipitate formed was filtered off, washed with ether and dried. Yield 0.95 g; $[\alpha]_D^{20} = 103.8°$ (c=1, DMF); melting point 123° C. decomposition.

3.

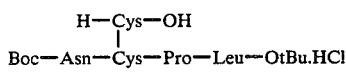

500 mg (0.71 millimole) of the peptide obtained in 2. were dissolved in 10 ml of trifluoroethanol after which 249 mg (1.42 millimoles) of cysteine.H$_2$O.HCl in 1 ml of methanol were added to this solution. After it had been stirred for 4 hours, the solution was evaporated and the residue was stirred with ether.

Yield 600 mg.

4.

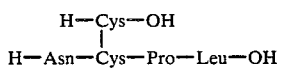

600 mg (±0.71 millimole) of the peptide obtained in 3. were dissolved in 10 ml of 90% strength TFA and the solution was stirred for 45 minutes at room temperature. The mixture was poured out into ether and the precipitate formed was filtered off, washed with ether and dried. This precipitate was dissolved in water and was subjected to exchange with an ion exchanger in the acetate form and then freeze-dried. This freeze-dried material was purified by counter-current distribution (system: BuOH/HOAc/water (4:1:5)). The substance thus obtained was further purified on a silica gel column.

Yield 200 mg.

Rf=0.18 in BuOH/Py/HOAc/water (8:3:1:4).

EXAMPLE 3

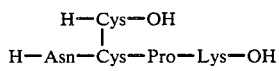

was prepared in a manner corresponding to Example 1 and

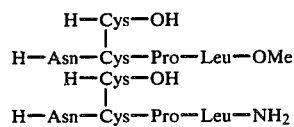

were prepared in a manner corresponding to Example 2.

EXAMPLE 4

1. (Boc-Asn-Cys-Pro-Leu-OtBu)$_2$ 500 mg (0.58 millimole) of Boc-Asn-Cys(Trt)-Pro-Leu-OtBu (Example 2.1) were dissolved in 127 ml of an 0.005 molar solution of iodine and the mixture was stirred for 1 hour. Thereafter sufficient 1N sodium thiosulphate was added to cause the brownish red colour to disappear. After adding 0.7 ml of 1N NaOH and 150 ml of water, a precipitate formed and this was filtered off. The residue was dissolved in methylene chloride after which it was precipitated again with ether/hexane (1:1), filtered off and dried.

Yield 310 mg.

Rf=0.70 in methylene chloride:MeOH:water (70:30:5) on SiO$_2$.

2.

300 mg (0.24 millimole) of the peptide obtained in 1. were dissolved in 10 ml of 90% TFA solution and the solution was stirred for 1 hour. It was poured out into ether and the precipitate formed was filtered off. This precipitate was redissolved in water, after which the solution was treated with an ion exchanger in the acetate form. Thereafter, the solution was further purified over a silica gel column, using BuOH:Py:HOAc:water (8:3:1:4) as the eluant.

Yield 105 mg.

Rf in the abovementioned solvent (eluant)=0.18 on SiO$_2$.

EXAMPLE 5

The peptide obtained in Example 1.1. was treated with iodine in the manner described in Example 4.1., after which the peptide

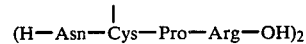

was obtained in the same manner as described in Example 1.4.

Rf in BuOH:HOAc:water (1:2:1)=0.20 on SiO$_2$.

The following were prepared in a corresponding manner:

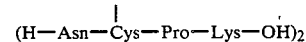

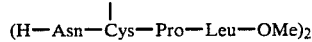

and

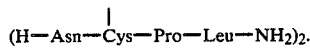
(H—Asn—Cys—Pro—Leu—NH₂)₂.

I claim:

1. Peptide having the general formula:

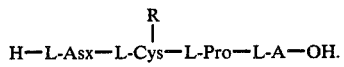
H—L-Asx—L-Cys—L-Pro—L-A—OH.

wherein A represents Arg, Lys or Leu and R represents the group

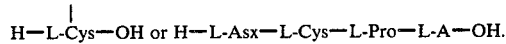
H—L-Cys—OH or H—L-Asx—L-Cys—L-Pro—L-A—OH.

2. A pharmaceutically acceptable derivative of the compound of claim 1 which is a salt; C1-6 N-acyl derivative of a carboxylic acid; an amide, a C1-6 monoalkylamide or di(C1-6 alkyl)amide; or an ester derived from a C1-18 alcohol.

3. A pharmaceutically acceptable derivative of the compound of claim 2 which is a salt; C1-6 N-acyl derivative of a carboxylic acid; an amide, a C1-6 monoalkylamide or di(C1-6 alkyl)amide; or an ester derived from a C1-18 alcohol.

4. A pharmaceutically acceptable derivative of the compound of claim 3 which is a salt; C1-6 N-acyl derivative of a carboxylic acid; an amide, a C1-6 monoalkylamide or di(C1-6 alkyl)amide; or an ester derived from a C1-18 alcohol.

5. Peptide according to claim 1, of the formula:

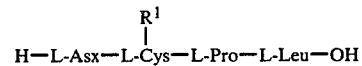
H—L-Asx—L-Cys—L-Pro—L-Leu—OH wherein $R^1$ represents

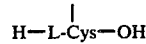
H—L-Cys—OH or the group

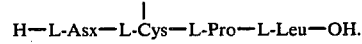
H—L-Asx—L-Cys—L-Pro—L-Leu—OH.

6. Peptide according to claim 1, of the formula:

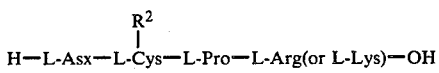
H—L-Asx—L-Cys—L-Pro—L-Arg(or L-Lys)—OH wherein $R^2$ represents the group

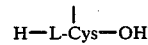
H—L-Cys—OH or the group

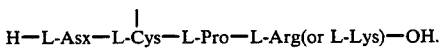
H—L-Asx—L-Cys—L-Pro—L-Arg(or L-Lys)—OH.

7. A pharmaceutical preparation for effecting memory function containing (i) a pharmaceutically effective amount of the peptide of claim 1 or a pharmaceutically acceptable derivative of the compound of claim 1 which is a salt; C1-6 N-acyl derivative of a carboxylic acid; an amide, a C1-6 monoalkylamide or di(C1-6 alkyl)amide; or an ester derived from a C1-18 alcohol; and (ii) in admixture therewith a carrier suitable for pharmaceutical administration.

* * * * *